United States Patent
Haye et al.

(10) Patent No.: US 10,436,728 B2
(45) Date of Patent: Oct. 8, 2019

(54) VIBRATION INDUCED NOISE SUPPRESSION DEVICE

(71) Applicant: UNITED TECHNOLOGIES CORPORATION, Farmington, CT (US)

(72) Inventors: Sheridon Everette Haye, Mansfield, CT (US); Jun Liu, Hartford, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 218 days.

(21) Appl. No.: 15/604,336

(22) Filed: May 24, 2017

(65) Prior Publication Data

US 2018/0340899 A1 Nov. 29, 2018

(51) Int. Cl.
| | |
|---|---|
| *G01N 27/02* | (2006.01) |
| *F01D 25/18* | (2006.01) |
| *F01D 21/00* | (2006.01) |
| *G01N 33/28* | (2006.01) |
| *H01F 5/04* | (2006.01) |
| *H01F 27/02* | (2006.01) |

(52) U.S. Cl.
CPC ......... *G01N 27/025* (2013.01); *F01D 21/003* (2013.01); *F01D 25/18* (2013.01); *G01N 33/2835* (2013.01); *G01N 33/2858* (2013.01); *H01F 5/04* (2013.01); *H01F 27/02* (2013.01); *F05D 2220/32* (2013.01); *F05D 2260/96* (2013.01)

(58) Field of Classification Search
None
See application file for complete search history.

(56) References Cited

U.S. PATENT DOCUMENTS

| | | | | |
|---|---|---|---|---|
| 5,001,424 A | * | 3/1991 | Kellett | F16N 29/00 324/204 |
| 5,444,367 A | | 8/1995 | Kempster et al. | |
| 5,811,664 A | * | 9/1998 | Whittington | G01N 15/0656 73/53.07 |
| 7,956,601 B2 | * | 6/2011 | Becker | G01N 33/2858 324/204 |
| 8,354,836 B2 | | 1/2013 | Becker et al. | |

(Continued)

FOREIGN PATENT DOCUMENTS

| | | |
|---|---|---|
| CA | 2639710 A1 | 3/2010 |
| EP | 2028474 A2 | 2/2009 |
| WO | 2007088015 A1 | 8/2007 |

OTHER PUBLICATIONS

European Search Report for European Application No. 18174174.5 dated Nov. 19, 2018, 7pages.

*Primary Examiner* — Peter J Macchiarolo
*Assistant Examiner* — Jermaine L Jenkins
(74) *Attorney, Agent, or Firm* — Cantor Colburn LLP

(57) ABSTRACT

A sensor for sensing debris in a lubrication flow through a lubrication channel in a gas turbine engine, the sensor including: a housing; external electronics communicating sensed data to a signal processor; internal electronics within the housing, the internal electronics being electronically connected to the external electronics, the internal electronics including a plurality of sensor coils adjacently disposed in a lubrication flow-wise direction; and internal damping material separating the plurality of sensor coils from the housing.

13 Claims, 3 Drawing Sheets

(56) References Cited

U.S. PATENT DOCUMENTS

| | | | |
|---|---|---|---|
| 8,522,604 B2* | 9/2013 | Zhe ...................... | G01M 13/02 324/204 |
| 2009/0189599 A1 | 7/2009 | Fujii et al. | |
| 2017/0138217 A1 | 5/2017 | Schwarz et al. | |

* cited by examiner

VIBRATION INDUCED NOISE SUPPRESSION DEVICE

BACKGROUND

Exemplary embodiments pertain to the art of noise suppression and more specifically to suppressing vibration induced noise in debris detecting sensors in a lubrication circuit of a gas turbine engine.

Debris sensors in lubrication circuits for gas turbine engines may be affected by vibrations induced from engine throttling. Such vibrations may resonate sensor coils resulting in signal noise in the sensed data rendering unreliable such data. Accordingly it is desirable to suppress vibrations induced in sensor coils to reduce signal noise in the sensed data.

BRIEF DESCRIPTION

Disclosed is a sensor for sensing debris in a lubrication flow through a lubrication channel in a gas turbine engine, the sensor comprising: a housing; external electronics communicating sensed data to a signal processor; internal electronics within the housing, the internal electronics being electronically connected to the external electronics, the internal electronics including a plurality of sensor coils adjacently disposed in a lubrication flow-wise direction; and internal damping material separating the plurality of sensor coils from the housing.

In addition to one or more of the features described above, or as an alternative, further embodiments may include that the internal damping material envelops the plurality of sensor coils.

In addition to one or more of the features described above, or as an alternative, further embodiments may include that the internal damping material extends axially between a distal end and a proximate end of the housing.

In addition to one or more of the features described above, or as an alternative, further embodiments may include that the internal damping material extends annularly about the perimeter of the housing.

In addition to one or more of the features described above, or as an alternative, further embodiments may include external damping material disposed on a first side and/or second side of the housing.

In addition to one or more of the features described above, or as an alternative, further embodiments may include external damping material disposed on the first side and the second side of the housing.

In addition to one or more of the features described above, or as an alternative, further embodiments may include that the external damping material is disk shaped.

In addition to one or more of the features described above, or as an alternative, further embodiments may include that the external damping material is shaped as a cylindrical plate.

Further disclosed is a gas turbine engine which may include one or more of the above disclosed features.

Further disclosed is a method of sensing debris in a lubrication flow through a lubrication channel in a gas turbine engine, the method comprising: monitoring for debris in the lubrication flow through the lubrication channel with a sensor disposed in the lubrication channel, the sensor having a plurality of sensor coils within a housing, wherein internal damping material separates the plurality of sensor coils from the housing; sensing debris in the lubrication flow as debris affects a magnetic flux electronically communicated between the sensor coils; generating an electronic signal indicative of debris detection; and electronically communicating the electronic signal to a signal processor. The method may further include one or more of the above disclosed features.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
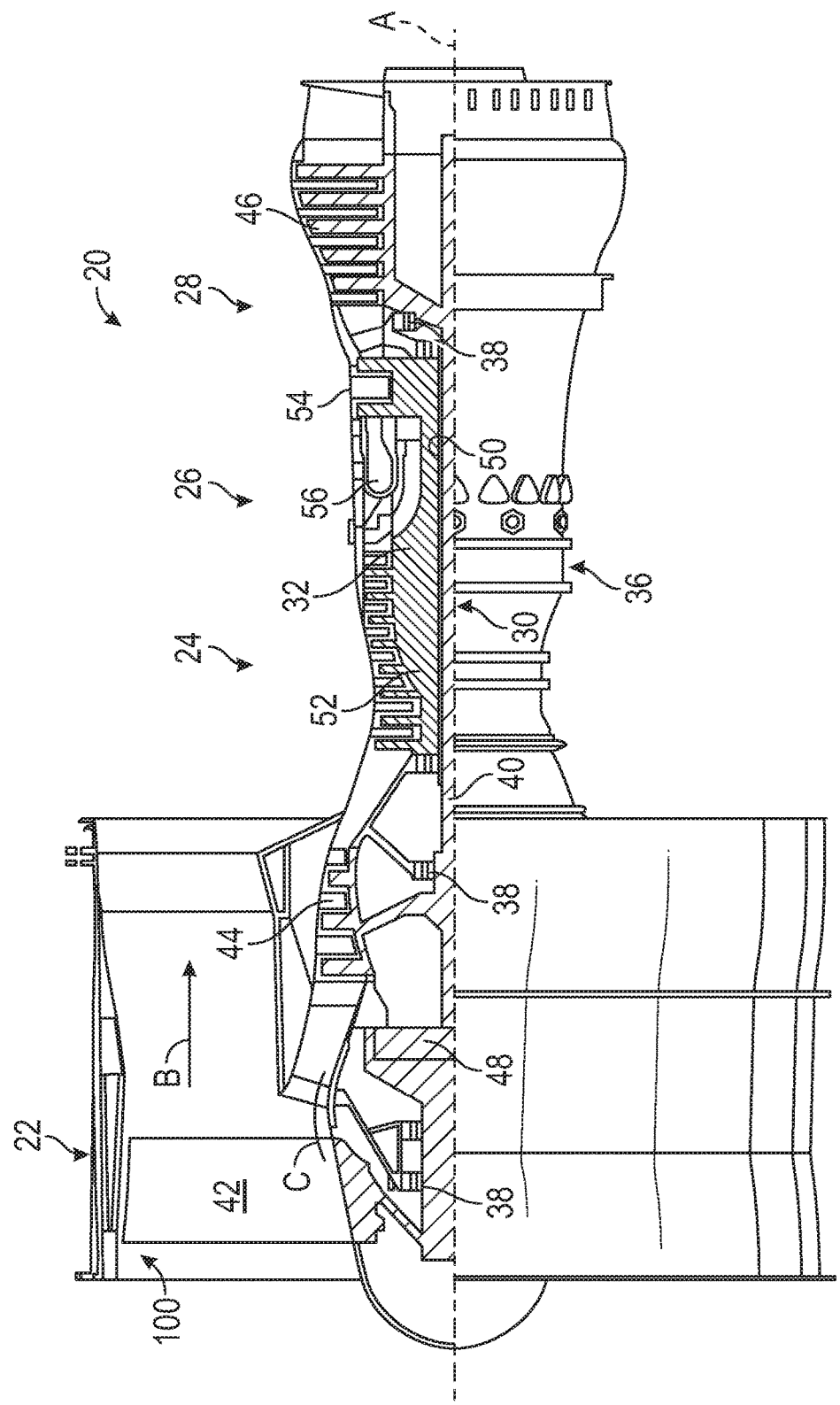
FIG. 1 is a partial cross sectional view of a gas turbine engine.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmenter section (not shown) among other systems or features. The fan section 22 drives air along a bypass flow path B in a bypass duct, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a low pressure compressor 44 and a low pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a high pressure compressor 52 and high pressure turbine 54. A combustor 56 is arranged in exemplary gas turbine 20 between the high pressure compressor 52 and the high pressure turbine 54. An engine static structure 36 is arranged generally between the high pressure turbine 54 and the low pressure turbine 46. The engine static structure 36 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present disclosure is applicable to other gas turbine engines including direct drive turbofans.

A significant amount of thrust is provided by the bypass flow B due to the high bypass ratio. The fan section 22 of the engine 20 is designed for a particular flight condition—typically cruise at about 0.8 Mach and about 35,000 feet (10,688 meters). The flight condition of 0.8 Mach and 35,000 ft (10,688 meters), with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of $[(Tram\ °\ R)/(518.7°\ R)]^{0.5}$. The "Low corrected fan tip speed" as disclosed herein according to one non-limiting embodiment is less than about 1150 ft/second (350.5 m/sec).

Figure 2A:
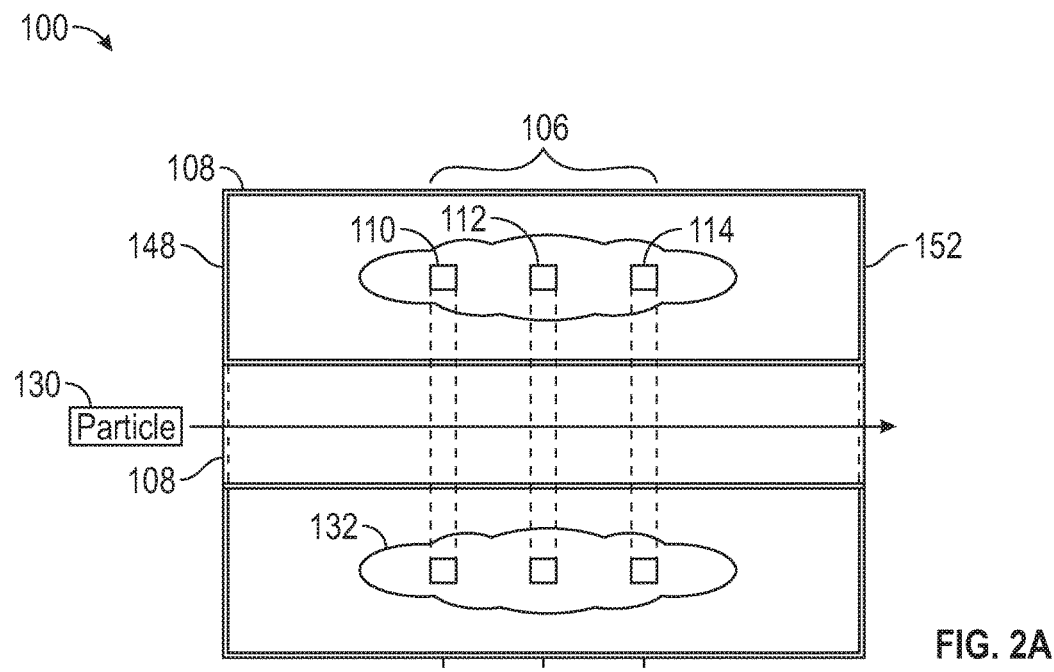
FIG. 2A is a schematic illustration of internal sensor electronics for a sensor according to one embodiment of the disclosure.
Figure 3:
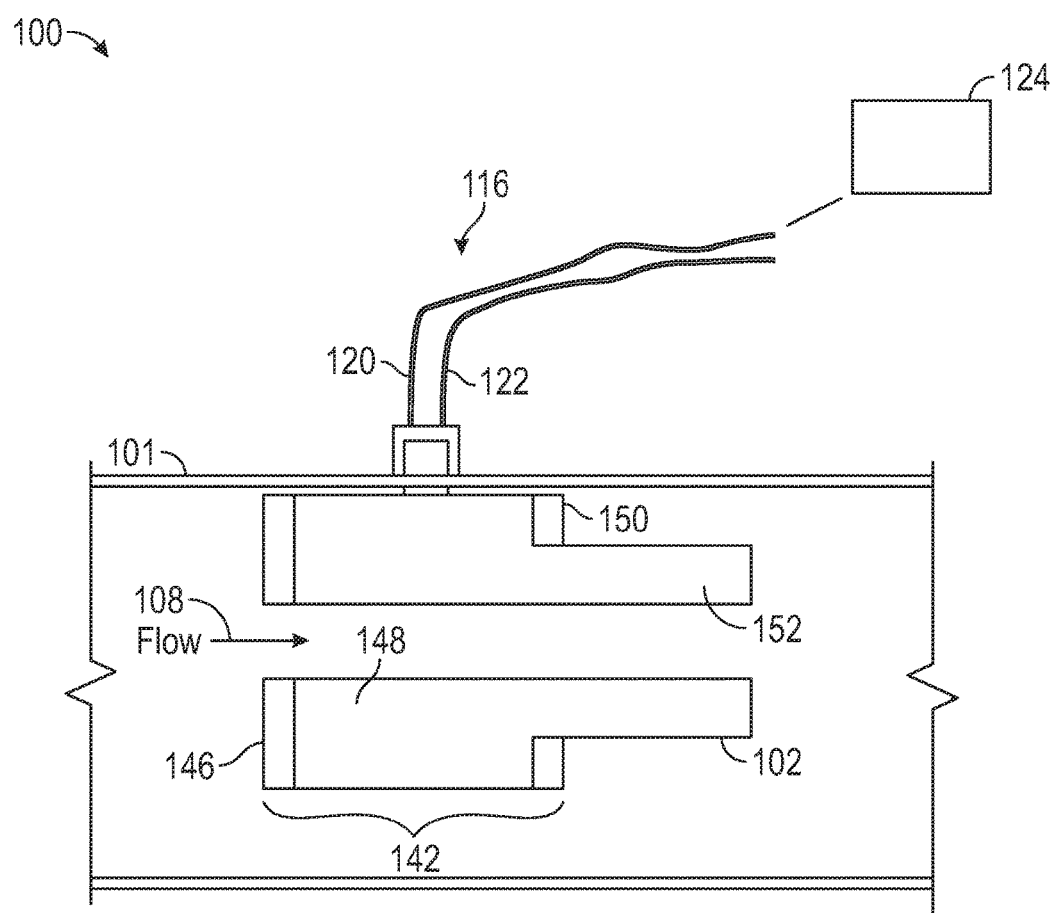
FIG. 3 is a schematic illustration of a sensor housing and external sensor electronics for a sensor according to one embodiment of the disclosure.

Turning now to FIGS. 2A and 3 disclosed is a sensor 100 for a gas turbine engine 20. The sensor 100 may be disposed in a lubrication system channel 101 such as a fluid lubrication system for example an oil lubrication system. The sensor 100 may be a particulate matter sensor for the lubrication system. Many types of sensors may be in the gas turbine engine 20 and many particulate sensors may be within the lubrication system channel 101. The sensor 100 may be mounted on an engine static support for example on the fan case in the fan section 22 for example at thirty degrees from top-dead-center.

The sensor 100 may have a housing 102 defined by an elongated cylindrical body. The housing 102 may extend in the fluid flow-wise direction 108 from a proximate or upstream end 148 of the housing 102 to a distal or downstream end 152 of the housing 102. Internal sensor electronics within the housing 102 may include a coil assembly having a plurality of sensor coils 106 that may be adjacently disposed in a fluid flow wise direction 108. The coil assembly 106 is illustrated as having three coils 110, 112, 114 each extending annularly along the internal perimeter of the housing, and each being mutually spaced along the axial length of the housing, but such is not intended to limit or define an actual number or configuration of coils required in a sensor. The sensor 100 may also include external electronics 116 which may include a plurality of electrical connectors for example a first conducting wire 120 and a second conducting wire 122. The external electronics 116 communicate between the internal electronics 103 and a remotely located signal processing unit 124.

Figure 2B:
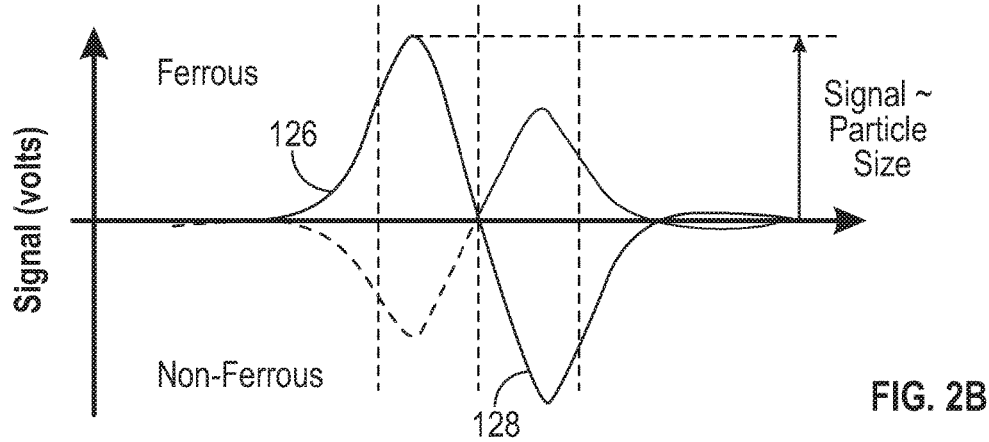
FIG. 2B is a graph of signals obtained from the sensor illustrated in FIG. 2A.

Sample sensor readings are illustrated in FIG. 2B which graphs output voltage on the abscissa and particle size on the ordinate. A first curve 126 represents the output sensor readings for ferrous particles and a second curve 128 represents output sensor readings for non-ferrous particles. The peak signals are obtained when larger particles for example particle 130 are sensed in the lubricant fluid.

Sensor readings may be affected by engine operations for example high throttle transient periods for example during takeoff and climb. During such operations, engine vibrations impacting the housing 102 cause relative movement or small displacements between the sensor coils 110-114 may eventually become electronic noise in the sensor signal. Such harmonics may also impact the external electronics 116 resulting in additional noise in the sensor readings.

As illustrated in FIG. 2A in one embodiment the internal electronics 106 may include internal damping material 132 that envelops the coils 110-114. The damping material 132 is disposed annularly about the internal perimeter of the housing and axially along the length of the housing 102 from the distal end 148 to the proximate end 152 and radially outside of the flow. The damping material 132 may absorb or reduce high frequency vibratory harmonics induced in the housing 102 by engine operations at high throttle before such harmonics reaches the coils. As illustrated in FIG. 3 in another embodiment the housing 102 may further include external damping material 142 to reduce vibratory harmonics in the internal electronics 106 and the external electronics 116 induced by engine operations. The damper material 142 may include proximate or upstream damper material 146 on or near a proximate or upstream end 148 of the housing 102 and distal or downstream damper material 150 on or near a distal or downstream end 152 of the housing 102. The housing 102 may be cylindrically shaped so that the external damping material 142 may be disk shaped to not disturb fluid flow about the sensor housing 101.

The term "about" is intended to include the degree of error associated with measurement of the particular quantity based upon the equipment available at the time of filing the application. For example, "about" can include a range of ±8% or 5%, or 2% of a given value.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A gas turbine engine comprising:
    a lubrication channel;
    a sensor disposed in the lubrication channel for sensing debris in a lubrication flow through the lubrication channel, the sensor comprising:
        a housing;
        external electronics connected to the housing and communicating sensed data to a signal processor;
        internal electronics within the housing, the internal electronics being electronically connected to the external electronics, the internal electronics including a plurality of sensor coils adjacently disposed in a lubrication flow-wise direction; and
        internal damping material separating the plurality of sensor coils from the housing.

2. The gas turbine engine of claim 1, wherein the internal damping material envelops the plurality of sensor coils.

3. The gas turbine engine of claim 1, wherein the internal damping material extends axially between a distal end and a proximate end of the housing.

4. The gas turbine engine of claim 3, wherein the internal damping material extends annularly about the perimeter of the housing.

5. The sensor of claim 1, comprising external damping material disposed on an upstream side and/or downstream side of the housing.

6. The gas turbine engine of claim 5, comprising external damping material disposed on the upstream side and the downstream side of the housing.

7. The gas turbine engine of claim 5, wherein the external damping material is disk shaped.

8. A method of sensing debris in a lubrication flow through a lubrication channel in a gas turbine engine, the method comprising:
    monitoring for debris in the lubrication flow through the lubrication channel with a sensor disposed in the lubrication channel, the sensor having a plurality of sensor coils within a housing, wherein internal damping material separates the plurality of sensor coils from the housing;
    sensing debris in the lubrication flow as debris affects a magnetic flux electronically communicated between the sensor coils;
    generating an electronic signal indicative of debris detection; and
    electronically communicating the electronic signal to a signal processor.

9. The method of claim 8, wherein the internal damping material envelops the plurality of sensor coils.

10. The method of claim 9, wherein the internal damping material extends axially between a distal end and a proximate end of the housing.

11. The method of claim 8, wherein the internal damping material extends annularly about the perimeter of the housing.

12. The method of claim 11, comprising external damping material disposed on at least one of a proximate end and a distal end of the housing.

13. The method of claim 12, comprising external damping material disposed on a proximate end and a distal end of the housing.

* * * * *